United States Patent
Gajji et al.

(10) Patent No.: US 10,495,558 B2
(45) Date of Patent: Dec. 3, 2019

(54) MULTI-SURFACE VISCOSITY MEASUREMENT

(71) Applicant: Halliburton Energy Services, Inc., Houston, TX (US)

(72) Inventors: Bhargav Gajji, Cypress, TX (US); Ketan Chimanlal Bhaidasna, Houston, TX (US); Richard Gary Morgan, Channelview, TX (US); Subrahmanyam Surya Venkata Sista, Hyderabad (IN)

(73) Assignee: Halliburton Energy Services, Inc., Houston, TX (US)

(*) Notice: Subject to any disclaimer, the term of this patent is extended or adjusted under 35 U.S.C. 154(b) by 363 days.

(21) Appl. No.: 15/543,045

(22) PCT Filed: Mar. 17, 2015

(86) PCT No.: PCT/US2015/021039
§ 371 (c)(1),
(2) Date: Jul. 12, 2017

(87) PCT Pub. No.: WO2016/148704
PCT Pub. Date: Sep. 22, 2016

(65) Prior Publication Data
US 2018/0003607 A1    Jan. 4, 2018

(51) Int. Cl.
*G01N 11/14* (2006.01)
*E21B 49/08* (2006.01)

(52) U.S. Cl.
CPC .............. *G01N 11/14* (2013.01); *E21B 49/08* (2013.01); *E21B 2049/085* (2013.01)

(58) Field of Classification Search
None
See application file for complete search history.

(56) References Cited

U.S. PATENT DOCUMENTS

| | | | | |
|---|---|---|---|---|
| 3,069,900 | A | * 12/1962 | Kimberly | E21B 21/08 73/54.32 |
| 3,777,551 | A | * 12/1973 | Weiss | E21B 21/08 73/54.28 |
| 4,299,118 | A | 11/1981 | Gau et al. | |
| 4,484,468 | A | 11/1984 | Gau et al. | |
| 4,557,142 | A | 12/1985 | Hensley et al. | |

(Continued)

FOREIGN PATENT DOCUMENTS

EP    0734515 B1    4/2002

OTHER PUBLICATIONS

International Preliminary Report on Patentability issued in related PCT Application No. PCT/US2015/021039 dated Sep. 19, 2017, 6 pages.

(Continued)

*Primary Examiner* — Jill E Culler
(74) *Attorney, Agent, or Firm* — Tenley Krueger; Baker Botts L.L.P.

(57) ABSTRACT

Systems and methods for measuring the viscosity of a fluid may comprise a rotor cup having an inner chamber; a first bob rotatably disposed within a first region of the inner chamber; and a second bob rotatably disposed within a second region of the inner chamber, wherein the second bob rotates relative to the first bob based on a difference in viscosity of fluid in the first region and the second region.

20 Claims, 3 Drawing Sheets

(56) References Cited

U.S. PATENT DOCUMENTS

| | | | | |
|---|---|---|---|---|
| 5,546,791 | A | * | 8/1996 | Meeten ................ G01N 11/14 73/54.28 |
| 6,629,451 | B1 | * | 10/2003 | Taylor .................... G01N 11/14 73/54.28 |
| 2001/0041400 | A1 | | 11/2001 | Boyle et al. |
| 2001/0042400 | A1 | | 11/2001 | Boyle et al. |

OTHER PUBLICATIONS

International Search Report and Written Opinion issued in related PCT Application No. PCT/US2015/021039 dated Dec. 3, 2015, 8 pages.

\* cited by examiner

MULTI-SURFACE VISCOSITY MEASUREMENT

CROSS-REFERENCE TO RELATED APPLICATION

The present application is a U.S. National Stage Application of International Application No. PCT/US2015/021039 filed Mar. 17, 2015, which is incorporated herein by reference in its entirety for all purposes.

BACKGROUND

The present disclosure relates generally to well drilling operations and, more particularly, to evaluate the properties of the fluids used in well drilling operations.

Hydrocarbons, such as oil and gas, are commonly obtained from subterranean formations that may be located onshore or offshore. The development of subterranean operations and the processes involved in removing hydrocarbons from a subterranean formation are complex. Typically, subterranean operations involve a number of different steps such as, for example, drilling a wellbore at a desired well site, cementing the well, treating the wellbore to optimize production of hydrocarbons, and performing the necessary steps to produce and process the hydrocarbons from the subterranean formation.

Various types of fluids are used in the oil and gas industry. Non-limiting examples include drilling muds, cement slurries, and stimulation treating fluids. Such fluids are typically pumped into oil or gas wells in known manners. It is desirable to know various characteristics of the fluids to determine how such fluids will act upon being pumped and placed in, or circulated through, the wells. For example, fluids used downhole are often exposed to unique conditions, including high pressures and temperatures.

Viscosity, elasticity, and consistency are rheological characteristics that sometimes need to be measured for a given fluid. Known devices used to test fluids for these characteristics include viscometers, rheometers, and consistometers. However, downhole pressures and temperatures may change the characteristics of a fluid. As a result, the fluid characteristics measured at the surface may be inconsistent with how the fluid behaves within the well environment. Fluids are typically chosen for an operation based on favorable properties, such as an ability to suspend particulates. It is therefore desirable to measure fluid properties, including viscosity, of a downhole fluid under downhole conditions before the fluid is placed in the well.

FIGURES

Some specific exemplary embodiments of the disclosure may be understood by referring, in part, to the following description and the accompanying drawings.

While embodiments of this disclosure have been depicted and described and are defined by reference to exemplary embodiments of the disclosure, such references do not imply a limitation on the disclosure, and no such limitation is to be inferred. The subject matter disclosed is capable of considerable modification, alteration, and equivalents in form and function, as will occur to those skilled in the pertinent art and having the benefit of this disclosure. The depicted and described embodiments of this disclosure are examples only, and not exhaustive of the scope of the disclosure.

DETAILED DESCRIPTION

For the purposes of this disclosure, computer-readable media may include any instrumentality or aggregation of instrumentalities that may retain data and/or instructions for a period of time. Computer-readable media may include, for example, without limitation, storage media such as a direct access storage device (e.g., a hard disk drive or floppy disk drive), a sequential access storage device (e.g., a tape disk drive), compact disk, CD-ROM, DVD, RAM, ROM, electrically erasable programmable read-only memory (EEPROM), and/or flash memory; as well as communications media such as wires, optical fibers, microwaves, radio waves, and other electromagnetic and/or optical carriers; and/or any combination of the foregoing.

Illustrative embodiments of the present disclosure are described in detail herein. In the interest of clarity, not all features of an actual implementation may be described in this specification. It will of course be appreciated that in the development of any such actual embodiment, numerous implementation-specific decisions are made to achieve the specific implementation goals, which will vary from one implementation to another. Moreover, it will be appreciated that such a development effort might be complex and time-consuming, but would, nevertheless, be a routine undertaking for those of ordinary skill in the art having the benefit of the present disclosure.

The terms "couple" or "couples" as used herein are intended to mean either an indirect or a direct connection. Thus, if a first device couples to a second device, that connection may be through a direct connection or through an indirect mechanical or electrical connection via other devices and connections. Similarly, the term "communicatively coupled" as used herein is intended to mean either a direct or an indirect communication connection. Such connection may be a wired or wireless connection such as, for example, Ethernet or LAN. Such wired and wireless connections are well known to those of ordinary skill in the art and will therefore not be discussed in detail herein. Thus, if a first device communicatively couples to a second device, that connection may be through a direct connection, or through an indirect communication connection via other devices and connections.

Figure 1A:
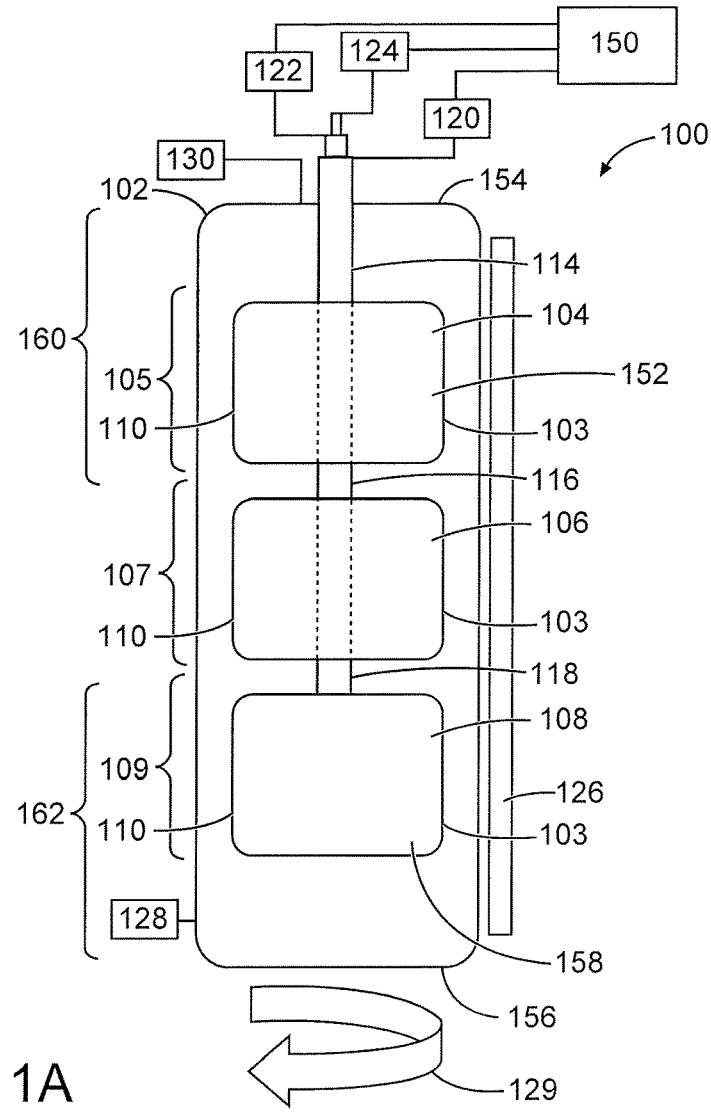
FIG. 1A is a diagram showing an illustrative viscosity measurement system comprising a plurality of bobs each connected to a shaft, according to aspects of the present disclosure.

FIG. 1A shows a viscosity measurement system 100. The system 100 may comprise a rotor cup 102 and a plurality of bobs 103 rotatably disposed within an inner chamber 101 of the rotor cup 102. The inner chamber 101 may comprise a plurality of regions 110, where each of the plurality of bobs 103 is located within one of the plurality of regions 110. In certain embodiments, the plurality of bobs 103 may comprise a first bob 104 rotatably disposed within a first region 105 and a second bob 106 rotatably disposed within a second region 107. In certain embodiments, the plurality of bobs 103 may comprise more than two bobs. For example, in certain embodiments, the plurality of bobs may further comprise a third bob 108 rotatably disposed within a third region 109 of the inner chamber 101 within the rotor cup 102.

In certain embodiments, the plurality of bobs 103 may comprise a proximate bob 152 and a distal bob 158. The proximate bob 152 may be located within a proximate region 160 adjacent to a rotor cup first end 154 and the distal bob 158 may be located in a distal region 162 adjacent to a rotor cup second end 156.

A fluid may be contained within the inner chamber 101. In certain embodiments, the fluid may comprise any fluid or combination of fluids for use in a down-hole environment. For example, the fluid may comprise a mud, oil well cements, and completion gels, and other fluids for use in the down-hole environment. In certain embodiments, the fluid may be a non-homogeneous fluid, a non-Newtonian fluid, a homogeneous fluid, a Newtonian fluid, or a combination of two or more such fluids.

The fluid may be in contact with the rotor cup 102 and the plurality of bobs 103. As such, rotation of the rotor cup 102 may cause rotation of the fluid within the inner chamber 101. Rotation of the fluid within the inner chamber 101 may cause rotation of one or more of the plurality of bobs 103. As will be described herein, the rotation properties of the plurality of bobs 103 in response to rotation of the rotor cup 102 may be a function of the fluid viscosity within the each of the plurality of regions 110. For example, if fluid within the first region 105 has a lower viscosity than fluid within the second region 107, the first bob 104 within the first region 105 will take longer to reach the rotational velocity of the rotor cup 102 than the second bob 106 within the second region 107. As such, the second bob may rotate at a different velocity relative to the first bob based on a difference in viscosity of fluid in the first region and the second region.

In certain embodiments, the first bob 104 may be connected to a first shaft 114 and the second bob 106 may be connected to a second shaft 116. In certain embodiments, a third bob 108 may be connected to a third shaft 118. In certain embodiments, the first bob 104 may be rotatably connected to the first shaft 114 and the second bob 106 may be rotatably connected to the second shaft. In certain embodiments, the first shaft 114 may rotate with the first bob 104 and the second shaft 116 may rotate with the second bob 106. As such, in certain embodiments, the second bob 106 may rotate independent of the first bob 104. However, in certain embodiments, the second bob may be connected directly to the first bob via a shaft or torque transducer, as described herein.

In certain embodiments, the first shaft 114 may be concentric with the second shaft 116. For example, the second shaft 116 may be disposed axially within the first shaft 114. The first shaft 114 may connect to the first bob 104 while the second shaft 116 may extend through the first bob 104 and connect to the second bob 106 (such extension through the first bob 104 is shown with dashed lines in FIG. 1A). In certain embodiments, the third shaft 118 may be concentric with the first shaft 114 and second shaft 116 and extend axially within the second shaft 116. The third shaft 118 may extend through the first bob 104 and the second bob 106 and connect to the third bob 108.

Each of the plurality of bobs 103 may rotate within the rotor cup 102 independently of one another. For example, a non-homogeneous fluid may be placed within the inner chamber. The non-homogeneous fluid may have a first viscosity within the first region 105 and a second viscosity within the second region 107. As a result, rotation of the non-homogeneous fluid around the first and second bobs 104, 106 may rotate the first bob 104 and the second bob 106 at different rotational velocities, and/or accelerate rotation of the first bob 104 at a different rate than the second bob 106. For example, for a non-homogeneous fluid having a viscosity that increases along the length of the rotor cup 102 (e.g., a fluid that comprises a particulate that settles in the fluid), the fluid may accelerate rotation of the distal bob 158 faster than rotation of the proximate bob 152.

In certain embodiments, the system 100 may comprise a first sensor 120 connected to the first shaft 114 and capable of detecting a first rotational property of the first bob 104 and a second sensor 122 connected to the second shaft 116 and capable of detecting a second rotational property of the second bob 106. In certain embodiments, the system 100 may further comprise a third sensor 124 connected to the third shaft 118 and capable of detecting a third rotational property of the third bob 108. For example, the first bob 104 may rotate the first shaft 114, where such rotation may be detected by the first sensor 120. The second bob 106 may rotate the second shaft 116, where such rotation may be detected by the second sensor 122. The sensors 120, 122, 124 may detect and/or measure rotational properties of the respective shaft the sensor is connected to, including rotational velocity and/or rotational acceleration. In certain embodiments, the rotational property of the shaft 114, 116, 118 may correlate to rotational properties of the respective bob 104, 106, 108 to which the shaft is connected (i.e., the rotational property of a shaft measured by a sensor may be imputed to the respective bob connected to that shaft).

Figure 2:
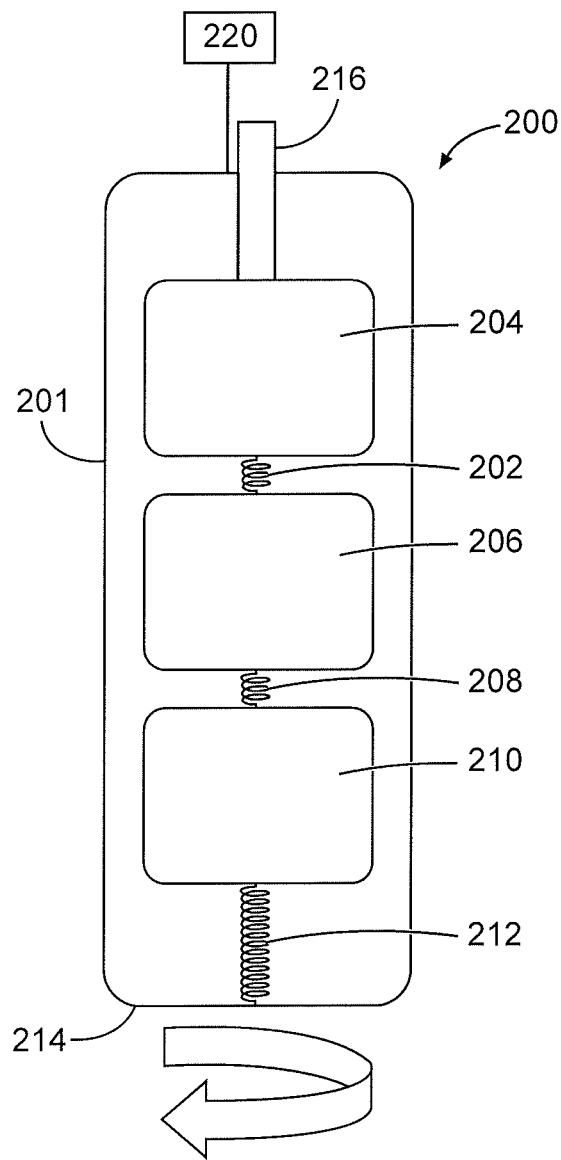
FIG. 2 is a diagraph showing an illustrative viscosity measurement system comprising a plurality of bobs connected by torque transducers, according to aspects of the present disclosure.

Referring now to FIG. 2, an embodiment of a viscosity measurement system 200 is shown comprising a rotor cup 201, a first torque transducer 202 connected to a proximate bob 204 and an intermediate bob 206, and a second torque transducer 208 connected to the intermediate bob 206 and a distal bob 210. In certain embodiments, an anchor torque transducer 212 may be connected to the distal bob 210 and a distal end 214 of the rotor cup 201. In certain embodiments, a shaft 216 may be connected to the proximate bob 204.

The torque transducers 202, 208, 212 may be rotatable. The first torque transducer 202 may allow the proximate bob 204 to rotate relative to the intermediate bob 206. As such, the proximate bob 204 may rotate at a different rotational velocity from the intermediate bob 206. The second torque transducer 208 may allow the intermediate bob 206 to rotate relative to the distal bob 210, where the intermediate bob 206 and distal bob 210 may have different rotational velocities. The anchor torque transducer 212 may allow the distal bob 210 to rotate relative to the rotor cup 201.

Each torque transducer 202, 208, 212 may allow a known amount of rotation in response to application of a known amount of torque. Each torque transducer may be tuned to rotate a desired amount in comparison to the maximum torque expected in view of the measurement resolution desired. For example, the first torque transducer 202 may allow 180° of rotation in response to 4 N·m of torque. For example, each torque transducer may be tuned such that the maximum expected torque rotates the torque transducer from between 10° and 360°. In certain embodiments, each torque transducer may allow the same rotation in response to applied torque. In other embodiments, each torque transducer may be tuned to different tensions to allow different rotation in response to an applied torque. In certain embodiments, the torque transducers may be in a parallel relationship, where the torque applied to each torque transducer is additive of the torque applied by all the bobs between the torque transducer and the distal end 214. For example, the torque applied to the first torque transducer 202 may be additive of the torque applied to each of the bobs between the proximate bob 204 and the distal end 214.

In certain embodiments, each torque transducer 202, 208, 212 may be wirelessly connected to a sensor 220. The sensor 220 may be capable of receiving data measurements indicative of the torque applied to each torque transducer 202, 208, 212.

Referring back to FIG. 1A, in certain embodiments, a heater 126 may be disposed adjacent to the rotor cup 102. The heater 126 may be capable of raising the temperature of the rotor cup 102 and/or fluid within the inner chamber 101. In certain embodiments, the heater 126 may raise the temperature of fluid within the inner chamber 101 to down-hole temperatures (i.e., the heater 126 may be capable of simulating down-hole environment temperatures). For example, the heater 126 may be capable of bringing the temperature of the rotor cup 102 and/or fluid within the inner chamber 101 within the range of 25° C. to 250° C.

In certain embodiments, a motor 128 may be connected to the rotor cup 102. The motor 128 may be capable of rotating the rotor cup 102 about the bob 104. For example, the motor 128 may axially rotate 129 the rotor cup 102 by applying a torque to the rotor cup 102. The motor 128 may be capable of rotating the rotor cup 102 at a constant angular velocity. For example, the motor 128 may rotate the rotor cup 102 at a set point velocity determined by an operator. In certain embodiments, the motor 128 may linearly accelerate the rotation of the rotor cup 102 until the angular velocity of the rotor cup 102 reaches the set point velocity, and then maintain the angular velocity of the rotor cup 102 at the set point velocity. In certain embodiments, the motor 128 may be capable of non-linearly accelerating the rotor cup 102 angular velocity (e.g., exponentially increasing the angular velocity of the rotor cup 102).

Figure 1B:
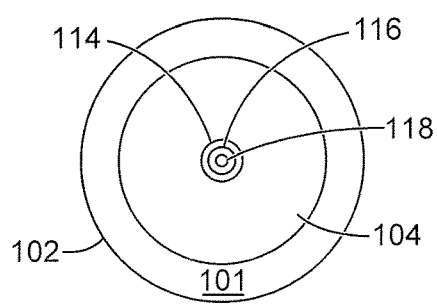
FIG. 1B is a top-down view of an illustrative viscosity measurement system, according to aspects of the present disclosure.

Referring now to FIG. 1B, a top-down view of the system 100 is shown comprising a first shaft 114, a second shaft 116, and, optionally, a third shaft 118 disposed within a rotor cup 102. In certain embodiments, the first shaft 114 may be concentric with the second shaft 116. For example, the second shaft 116 may be disposed axially within the first shaft 114. The first shaft 114 may connect to the first bob while the second shaft 116 may extend through the first bob and connect to the second bob.

In certain embodiments, the system 100 may comprise a pump 130 connected to the rotor cup 102. The pump connection may comprise one or more seals. The pump 130 may be capable of increasing or decreasing the pressure within the inner chamber 101. In certain embodiments, the rotor cup 102 may be capable of containing a pressure of between 0.5 atmosphere and 250 atm. For example, in certain embodiments, the inner chamber 101 may be pressurized to at least 2 atm by increasing pressure with the pump 130. In certain embodiments, the inner chamber 101 may be capable of containing a pressure of up to 500 atm.

In certain embodiments, a fluid may be contained within the rotor cup 102, within the rotor cup 102, where the fluid may be in contact with the first bob 104 and the second bob 106. The motor 128 may axially rotate the rotor cup 102 around the first bob 104 and the second bob 106. Axially rotating the rotor cup 102 may cause rotation of the fluid within at least the first region 105 and the second region 107 of the inner chamber 101, relative to the first bob 104 and the second bob 106, respectfully. For example, rotation of the rotor cup 102 may impart an angular shear force on the fluid, causing the fluid within the inner chamber 101 to rotate in the same angular direction as the rotor cup 102. The fluid moving within the first region 105 may exert a shear force on the first bob 104 and fluid moving within the second region 107 may exert a shear force on the second bob 106. As such, angular rotation of the first bob 104 and the second bob 106 may be independent from one another, and dependent on the ability of the fluid within each of the plurality of regions 110 to exert shear force on the respective bob within each region. This application of shear force to the fluid by the rotor cup 102 and/or by the fluid on each of the plurality of bobs 103 may be dependent on the viscosity of the fluid in contact with each bob. For example, greater viscosity of the fluid within the first region 105, may provide greater ability of the fluid to exert shear force to the first bob 104, which would lower the delay of the bob to match the set point angular velocity of the rotor cup 102. On the other hand, lower viscosity of fluid within one of the plurality of regions 110 would reduce the force exerted by the fluid on the respective bob or on the fluid by the rotor cup, thereby causing a relatively slower angular acceleration of the respective bob, where the respective bob would then take longer to reach a set point angular velocity of the rotor cup 102.

In certain embodiments, shear force exerted onto one of the plurality of bobs 103 by the fluid may cause that bob to rotate, which in turn may cause the respective shaft connected to that bob to rotate. For example, rotation of the first bob 104 may cause the first shaft 114 to rotate. Rotation of the first shaft 114 be detected and/or measured by the first sensor 120 connected to the first shaft 114. This description of the rotation of the first bob 104 may apply equally to each bob of the plurality of bobs where each bob is independent of the others. As such, the first bob of this description may be substituted for any other bob mentioned herein (i.e., the distal bob or the proximate bob may operate the same way).

The first sensor 114 may send measurement data containing detected rotation measurement information of the first shaft 114 to a processor 150. In certain embodiments, each of the sensors 114, 116, 118 may comprise a processor. In other embodiments, the processor 150 may be part of a computer separate from the sensors 114, 116, 118. For example, the processor 150 may be in communication with and capable of receiving measurement data in real-time from the sensors 114, 116, 118. Also for example, the measurement data may be sent to the processor 150 on a delayed basis, e.g., the measurement data may be sent to the processor 150 after the measurement data has been completely collected by the sensors 114, 116, 118. The processor 150 may be configured to generate at least one human readable output using the measurement data. For example, the processor 150 may output measurement data (e.g., instantaneous angular velocity, angular velocity over time, and/or angular displacement with respect to torque measurement), and/or manipulate the measurement data to output calculated viscosity.

In certain embodiments, one or more fluids having known fluid properties, such as viscosity, may be used to calibrate the system 100. After calibration, fluids having unknown viscosity properties may be measured by the system 100. Measurements observed by the sensors 114, 116, 118 for fluids having unknown properties may be compared to measurements from known fluids to determine to which known fluid the unknown fluid is most similar, in terms of viscosity profile.

Figure 3:
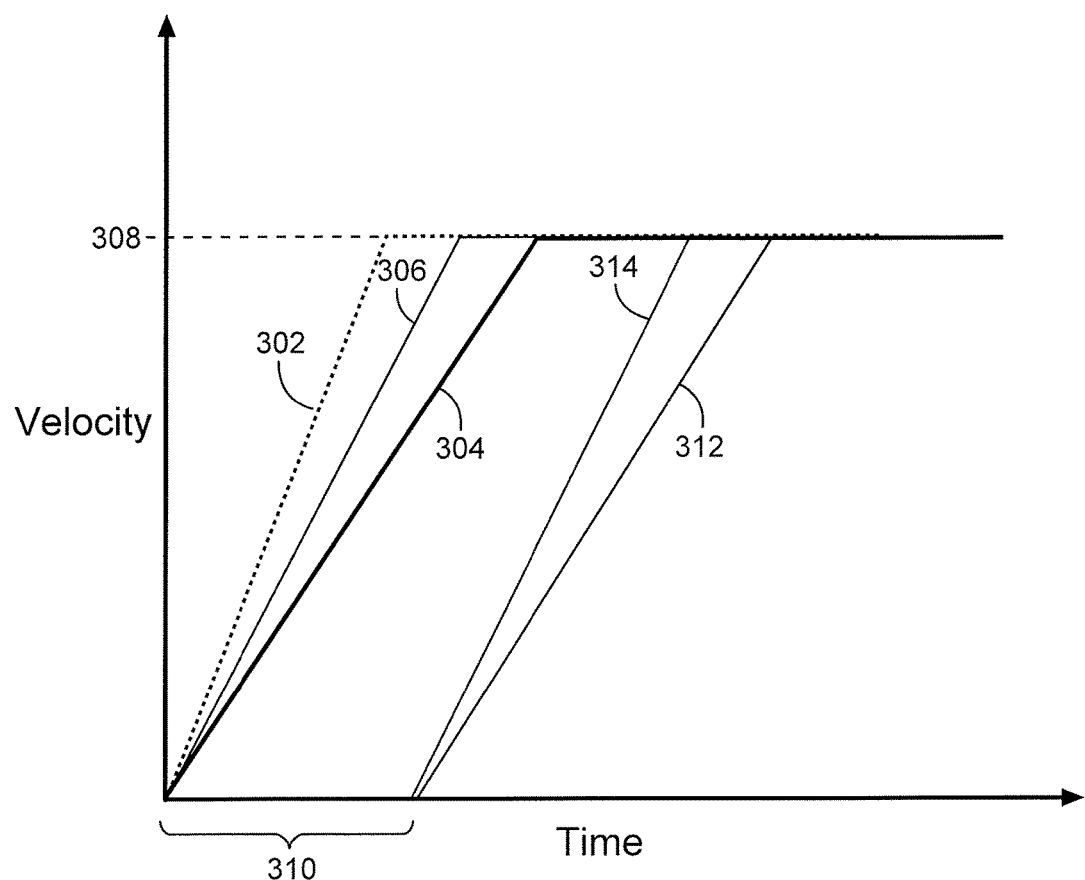
FIG. 3 is a graph illustrating a relationship of velocity of a rotor and a bob over time, according to aspects of the present disclosure.

Referring now to FIG. 3, an illustrative graph of angular velocity of a rotor cup over time 302, angular velocity of a proximate bob over time 304, and angular velocity of a distal bob over time 306 is shown, for a non-homogeneous fluid having a higher viscosity in a distal region than in a proximate region. For a system comprising one or more torque transducers, the torque output may be plot versus time and/or versus velocity of the rotor cup. In certain embodiments, a motor may increase the angular velocity of the rotor cup containing a fluid. For example, as shown in FIG. 3, the motor may linearly increase the angular velocity of the rotor cup 302 (i.e., apply constant angular acceleration to the rotor cup). Axial rotation of the rotor cup may rotate the fluid within the rotor cup (e.g., by imparting a shear force to the fluid). In certain embodiments, the motor may increase the angular velocity of the rotor cup up to a rotation velocity set point 308. The rotation velocity set point 308 may be determined by an operator. For example, in certain embodiments, the rotation velocity set point 308 may be from about 1 rotation per hour to about 1000 rotations per minute (rpm).

The fluid may be in contact with at least the proximate bob and the distal bob within the rotor cup and cause each bob to rotate within the rotor cup (e.g., by exerting a shear force on the bob). Each bob may rotate in response to the rotating fluid within the rotor cup. In certain embodiments, the angular velocity of each bob may increase slower than the rotor cup (i.e., each bob may have a lower angular acceleration than the rotor cup). The angular acceleration of the proximate bob may depend on the viscosity of the fluid within the proximate region and the angular acceleration of the distal bob may depend on the viscosity of the fluid within the distal region, where the viscosity may vary within the rotor cup, for example due to fluid settling. For example, as shown in FIG. 3, the angular velocity of the distal bob, shown by curve 306, may increase faster than the angular velocity of the proximate bob, shown by curve 304. Thus, in this example, the fluid within the distal region in contact with the distal bob may be shown to a higher viscosity than the fluid within the proximate region in contact with the proximate bob. In addition, such a fluid would be non-homogeneous. The angular velocity of each bob may increase until it reaches the rotation velocity set point 308, where the angular velocity of the bob may be substantially the same as the angular velocity of the rotor cup.

In certain embodiments, a shaft connected to one of the plurality of bobs may be held in place and substantially prevent the respective bob from rotating within the inner chamber. For example, the proximate bob and the distal bob may be held in place within the rotor cup during a rotor cup ramp up period 310. During the rotor cup ramp up period 310, the rotor cup may be axially rotated while one or more of the plurality of bobs are substantially prevented from rotating. In certain embodiments, the rotor cup ramp up period 310 may be any amount of time delay between starting rotation of the rotor cup and releasing the bob. For example, the rotor cup ramp up period 310 may provide a set time delay (i.e., head start) between rotor cup rotation and allowing the bob to rotate within the rotor cup. For example, the rotor cup ramp up period 310 allow the rotor cup to be increased to the rotational velocity set point 308. During the rotor cup ramp up period 310, the fluid may begin rotating within the inner chamber in response to a shear force imparted by the rotor cup. At the end of the ramp up period, the plurality of bobs may be released and allowed to rotate. After the rotor cup ramp up period 310, the angular velocity of the proximate bob over time 312 and the angular velocity of the distal bob over time 314 may be measured by a proximate bob sensor and a distal bob sensor, respectfully.

Although FIG. 2 shows linearly increasing the angular velocity of the rotor cup, non-constant acceleration may be applied to the rotor cup causing the angular velocity of the rotor cup to increase exponentially, geometrically, or other velocity profiles.

In other embodiment, each bob connected via independent torque sensors may respond with different torque measurements during ramp up in velocity of the rotor cup 102. Such varied torque measurements indicates non-homogeneity of the fluid along the length of the rotor cup 102. This difference can be observed over time to correlate to the rate of setting of particles within the fluid under constant shear similar to those in well bore scenarios. This information may be used by operators for wellbore job preplanning, such as in drilling or cementing operations.

Therefore, the present disclosure is well adapted to attain the ends and advantages mentioned as well as those that are inherent therein. The particular embodiments disclosed above are illustrative only, as the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered or modified and all such variations are considered within the scope and spirit of the present disclosure. Also, the terms in the claims have their plain, ordinary meaning unless otherwise explicitly and clearly defined by the patentee. The indefinite articles "a" or "an," as used in the claims, are defined herein to mean one or more than one of the element that it introduces.

What is claimed is:

1. A system for measuring the viscosity of a fluid, comprising:
   a rotor cup having an inner chamber;
   a first bob rotatably disposed within a first region of the inner chamber; and
   a second bob rotatably disposed within a second region of the inner chamber, wherein the second bob rotates relative to the first bob based on a difference in viscosity of fluid in the first region and the second region.

2. The system of claim 1, wherein the first bob is connected to a first shaft and the second bob is connected to a second shaft.

3. The system of claim 2, wherein the first shaft is concentric to the second shaft.

4. The system of claim 2, further comprising a first sensor connected to the first shaft capable of detecting a first property of the first bob and a second sensor connected to the second shaft capable of detecting a second property of the second bob.

5. The system of claim 1, further comprising a torque transducer connecting the first bob to the second bob.

6. The system of claim 1, further comprising a motor capable of rotating the rotor cup about the first bob and the second bob.

7. The system of claim 1, further comprising a heater disposed adjacent to the rotor cup capable of heating the rotor cup and fluid contained therein.

8. The system of claim 1, wherein the fluid includes a non-homogeneous fluid.

9. A method for measuring the viscosity of a fluid, comprising:
containing the fluid within a rotor cup having a first bob rotatably disposed within a first region of the rotor cup and a second bob rotatably disposed within a second region of the rotor cup;
rotating the rotor cup and the fluid disposed therein;
sensing a first property of the first bob;
sensing a second property of the second bob;
determining a first viscosity of the fluid in the first region based on the first property of the first bob; and
determining a second viscosity of the fluid in the second region based on the second property of the second bob.

10. The method of claim 9, wherein the first property includes a first angular acceleration of the first bob and the second property includes a second angular acceleration of the second bob.

11. The method of claim 9, wherein the first property includes a first torque of the first bob and the second property includes a second torque of the second bob.

12. The method of claim 9, wherein the fluid is a non-homogeneous fluid.

13. The method of claim 9, further comprising heating the rotor cup and fluid contained therein.

14. A viscometer, comprising:
a rotor cup;
a plurality of bobs rotatably disposed within the rotor cup, wherein the plurality of bobs includes a proximate bob and a distal bob;
a plurality of measurement regions defined within the rotor cup, wherein discrete bobs are disposed within discrete measurement regions; and
a first sensor capable of detecting a first property of the proximate bob indicative of the viscosity of the fluid within a proximate measurement region and a second sensor capable of detecting a second property of the distal bob indicative of the viscosity of the fluid within a distal measurement region.

15. The viscometer of claim 14, wherein the proximate bob is connected to a first shaft and the distal bob is connected to a second shaft, and wherein the second shaft is concentric to the first shaft.

16. The viscometer of claim 14, wherein the proximate bob and the distal bob are connected via at least one torque transducer.

17. The viscometer of claim 16, further comprising an anchor torque transducer connected to the distal bob and a rotor cup inner wall located at an opposite end from the proximate bob.

18. The viscometer of claim 14, further comprising a non-homogeneous fluid disposed within the rotor cup.

19. The viscometer of claim 14, wherein each of the plurality of bobs is axially aligned with one another and extend along a length of the rotor cup.

20. The viscometer of claim 14, wherein the first and second sensors are capable of detecting a rotational property of each of the plurality of bobs.

* * * * *